US012636112B2

(12) United States Patent
Mundahl et al.

(10) Patent No.: US 12,636,112 B2
(45) Date of Patent: May 26, 2026

(54) STRUCTURES FOR INTRACORPOREAL SPACING AND METHODS OF USING SAME

(71) Applicant: Boston Scientific Scimed, Inc., Maple Grove, MN (US)

(72) Inventors: John Mundahl, Golden Valley, MN (US); Benjamin R. Hoenes, St. Louis Park, MN (US); Sriharsha Mushnoori, Minneapolis, MN (US); Hak Rae Lee, Minneapolis, MN (US); John J. LaRoy, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1439 days.

(21) Appl. No.: 17/196,222

(22) Filed: Mar. 9, 2021

(65) Prior Publication Data

US 2021/0282882 A1 Sep. 16, 2021

Related U.S. Application Data

(60) Provisional application No. 62/987,449, filed on Mar. 10, 2020.

(51) Int. Cl.
*A61B 90/00* (2016.01)
*A61B 17/00* (2006.01)
(Continued)

(52) U.S. Cl.
CPC .............. *A61B 90/04* (2016.02); *A61L 27/16* (2013.01); *A61L 27/18* (2013.01); *A61L 27/52* (2013.01);
(Continued)

(58) Field of Classification Search
CPC ........... A61B 90/04; A61B 2090/0436; A61B 2090/0463; A61B 2090/0472;
(Continued)

(56) References Cited

U.S. PATENT DOCUMENTS 8,551,132 B2   10/2013   Eskridge et al.
9,682,251 B2    6/2017   Munro, III et al.
(Continued)

FOREIGN PATENT DOCUMENTS

WO         2019184554 A1   10/2019

OTHER PUBLICATIONS

International Search Report and Written Opinion for the International Patent Application No. PCT/US2021/021483, mailed Jun. 28, 2021, 17 pages.
(Continued)

*Primary Examiner* — Carrie R Dorna
*Assistant Examiner* — Joshua Daryl D Lannu
(74) *Attorney, Agent, or Firm* — Seager, Tufte & Wickhem LLP

(57) ABSTRACT

In some aspects, the present disclosure pertains to hydrogel-securing structures that comprise anchoring element that is configured to anchor the structure to bodily tissue and a hydrogel-retaining element that is configured to retain a hydrogel mass. Other aspects of the present disclosure include kits that contain such hydrogel-securing structures. Other aspects of the present disclosure pertain to methods that comprise (a) delivering a structure that comprises a hydrogel-retaining element in a body of a subject comprising first and second tissues, such that the hydrogel-retaining element may be disposed between the first tissue of tissue and the second tissue and (b) delivering a hydrogel to the structure, such that the hydrogel is loaded onto and/or into the hydrogel-retaining element and retained in place by the hydrogel-retaining element, and such that the hydrogel is disposed between the first and second tissues thereby separating the first tissue from the second tissue.

19 Claims, 5 Drawing Sheets

130b

110b

110a

Post-Injection

(51) Int. Cl.

| | |
|---|---|
| *A61B 17/064* | (2006.01) |
| *A61B 17/068* | (2006.01) |
| *A61L 27/16* | (2006.01) |
| *A61L 27/18* | (2006.01) |
| *A61L 27/52* | (2006.01) |
| *A61L 31/14* | (2006.01) |
| *A61N 5/10* | (2006.01) |

(52) U.S. Cl.
CPC ........ *A61N 5/10* (2013.01); *A61B 2090/0436* (2016.02); *A61B 2090/0463* (2016.02); *A61B 2090/0472* (2016.02); *A61B 2090/0481* (2016.02); *A61L 2400/06* (2013.01); *A61N 2005/1094* (2013.01); *A61N 2005/1096* (2013.01)

(58) Field of Classification Search
CPC .......... A61B 2090/0481; A61B 17/068; A61B 2017/00867; A61B 2017/00898; A61B 2017/00951; A61B 2017/0641; A61B 2017/0649; A61B 2090/0445; A61B 2090/3908; A61B 2090/3966; A61L 27/16; A61L 27/18; A61L 27/52; A61L 2400/06; A61L 31/145; A61L 2400/16; A61N 5/10; A61N 2005/1094; A61N 2005/1096

See application file for complete search history.

(56) References Cited

U.S. PATENT DOCUMENTS

| | | | | |
|---|---|---|---|---|
| 2004/0109823 | A1* | 6/2004 | Kaplan | ................... A61L 31/02 600/1 |
| 2004/0133275 | A1 | 7/2004 | Mansmann | |
| 2005/0267510 | A1* | 12/2005 | Razack | ............ A61B 17/12172 606/200 |
| 2009/0280182 | A1 | 11/2009 | Beck et al. | |
| 2011/0022164 | A1 | 1/2011 | Quinn et al. | |
| 2014/0378739 | A1* | 12/2014 | Munro, III | .......... A61N 5/1007 29/428 |
| 2015/0007827 | A1* | 1/2015 | Ozdil | ........................ A61F 6/22 128/831 |
| 2015/0148837 | A1* | 5/2015 | Shinar | .............. A61B 17/12036 606/200 |
| 2015/0314035 | A1* | 11/2015 | Rolfes Meyering | ... A61N 5/062 514/44 R |

| | | | |
|---|---|---|---|
| 2016/0089472 | A1 | 3/2016 | Bennett et al. |
| 2016/0325010 | A1* | 11/2016 | Liebler ................... A61L 24/08 |
| 2019/0069949 | A1 | 3/2019 | Vrba et al. |
| 2019/0143143 | A1 | 5/2019 | Abdalla |

OTHER PUBLICATIONS

Chung et al., "Dose escalation in locally advanced pancreatic cancer patients receiving chemoradiotherapy" Radiother Oncol. Jun. 2017;123(3):438-445.

Ma et al., "Dose escalation of radiation therapy with or without induction chemotherapy for unresectable locally advanced pancreatic cancer" Radiation Oncology vol. 13, Article No. 214 (2018).

Tee et al., "Indications and Perioperative Outcomes for Pancreatectomy with Arterial Resection" vol. 227, Issue 2, Aug. 2018, pp. 255-269.

Krishnan et al., "Focal Radiation Therapy Dose Escalation Improves Overall Survival in Locally Advanced Pancreatic Cancer Patients Receiving Induction Chemotherapy and Consolidative Chemoradiation" Int J Radiat Oncol Biol Phys. Mar. 15, 2016; 94(4): 755-765.

Hiroshima et al., "Concurrent chemoradiotherapy using proton beams for unresectable locally advanced pancreatic cancer-"Radiotherapy and Oncology—vol. 136, Jul. 2019, pp. 37-43.

Hoyer et al., "Phase-II study on stereotactic radiotherapy of locally advanced pancreatic carcinoma" Radiotherapy and Oncologyvol. 76, Issue 1, Jul. 2005, pp. 48-53.

Reyngold et al., ""Ablative radiation therapy for locally advanced pancreatic cancer: techniques and results"" Radiat Oncol. Jun. 6, 2019;14(1):95.

Han et al., "Tough, self-healable and tissue-adhesive hydrogel with tunable multifunctionality" NPG Asia Materials vol. 9, p. 372 (2017).

Bhagat et al., "Degradable Adhesives for Surgery and Tissue Engineering" Biomacromolecules 2017, 18, 10, 3009-3039.

Peterson et al., "Biodegradable Shape Memory Polymers in Medicine" Sep. 2017Advanced Healthcare Materials 6(21).

Sol Cabrera et al., "Computationally Designed 3D Printed Self-Expandable Polymer Stents with Biodegradation Capacity for Minimally Invasive Heart Valve Implantation: A Proof-of-Concept Study" 3D Printing and Additive Manufacturingvol. 4, No. 1—Mar. 1, 2017.

Jia et al., "3D printed self- expandable vascular stents from biodegradable shape memory polymer" Adv Polym Technol. 2018;37:3222-3228.

Zheng et al., "Biocompatible Shape Memory Blend for Self-Expandable Stents with Potential Biomedical Applications" ACS Appl. Mater. Interfaces 2017, 9, 16, 13988-13998.

* cited by examiner

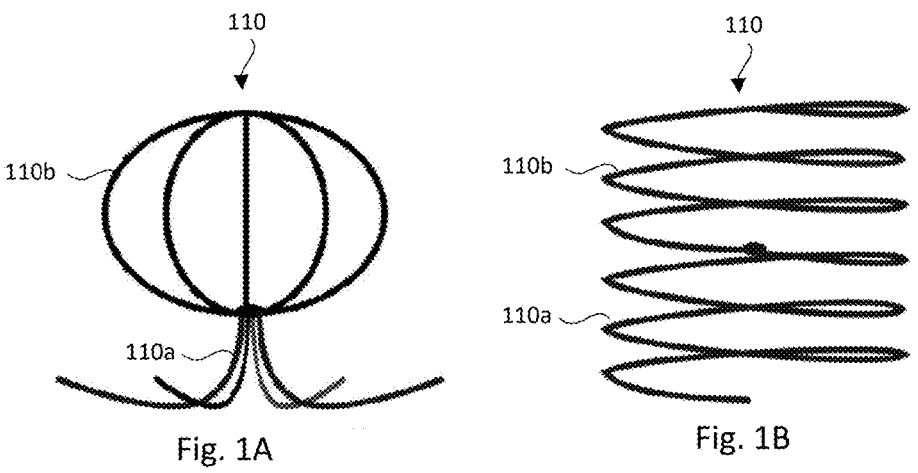
Fig. 1A                    Fig. 1B
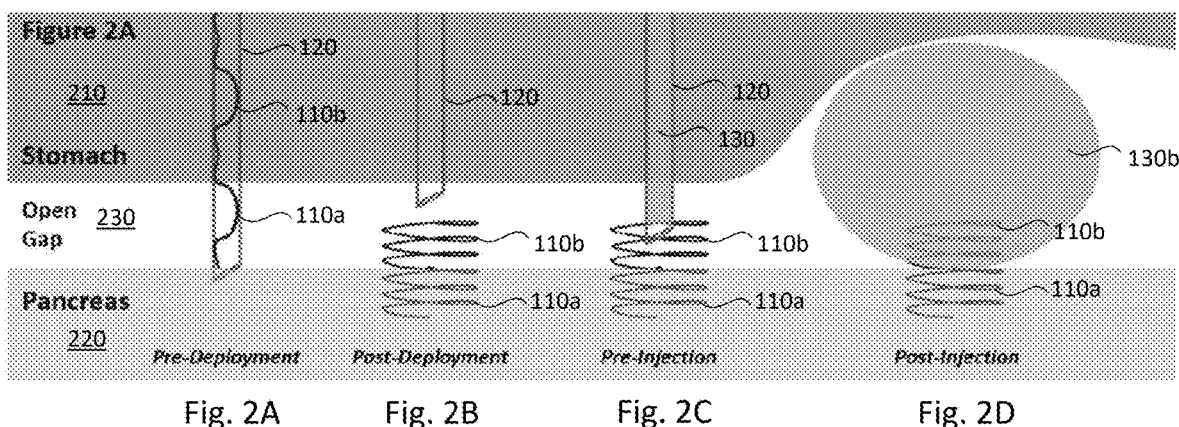
Fig. 2A      Fig. 2B      Fig. 2C      Fig. 2D
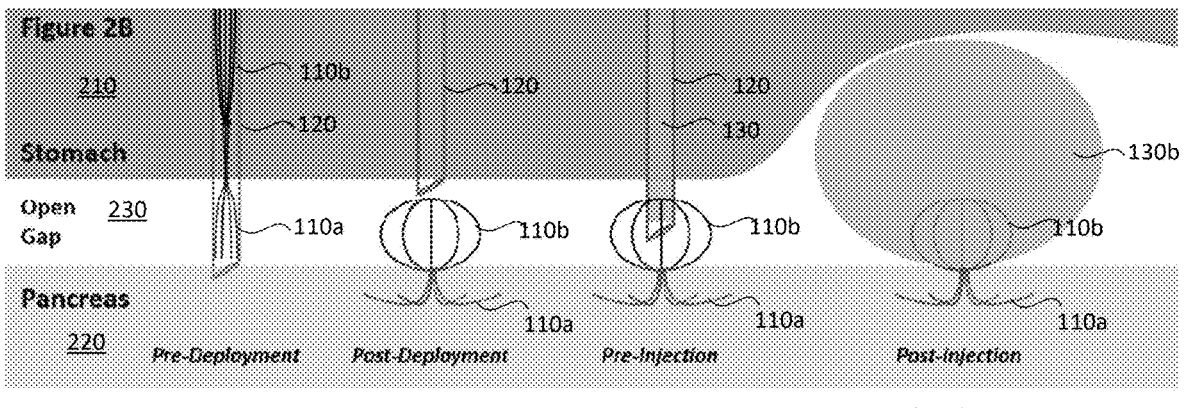
Fig. 3A      Fig. 3B      Fig. 3C      Fig. 3D

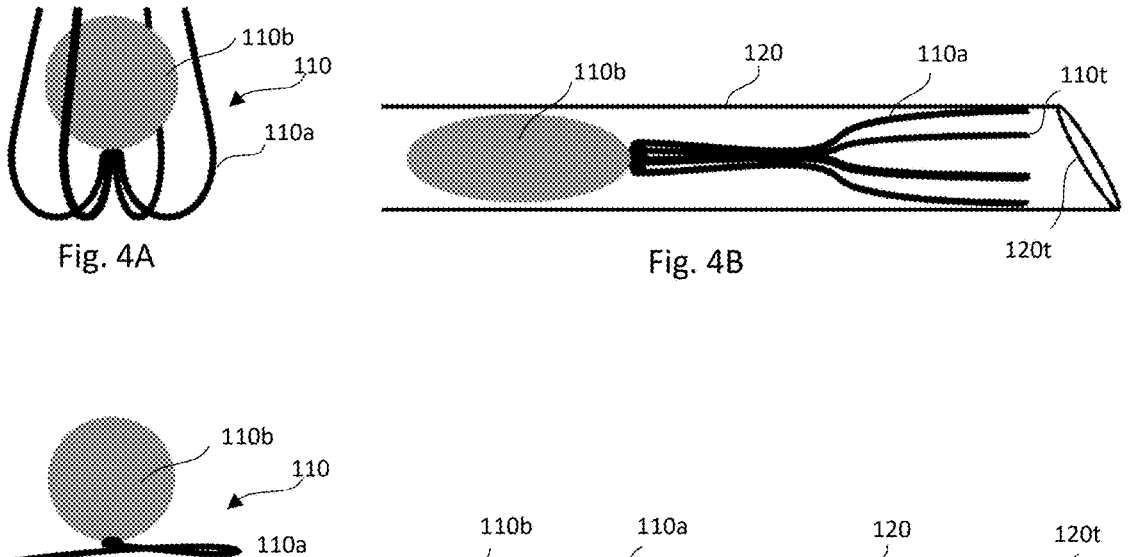
Fig. 4A
Fig. 4B
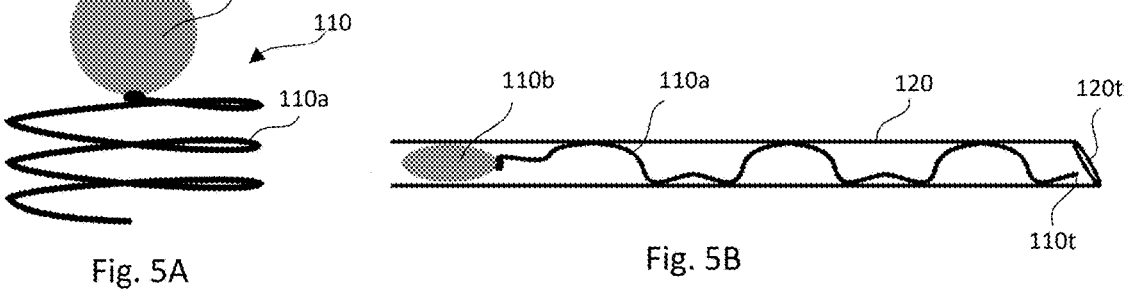
Fig. 5A
Fig. 5B
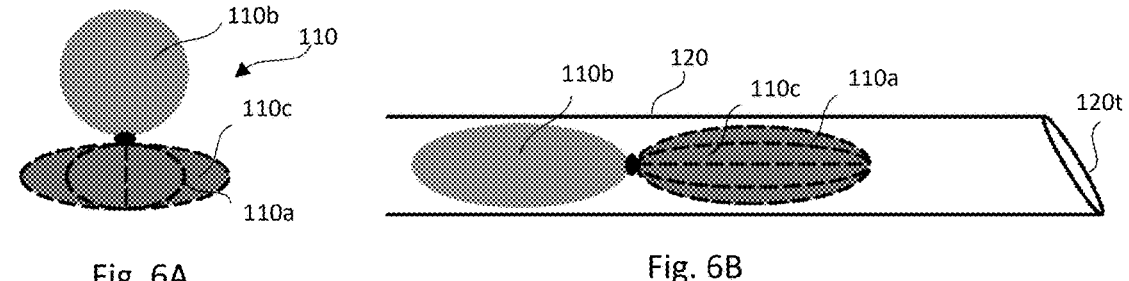
Fig. 6A
Fig. 6B

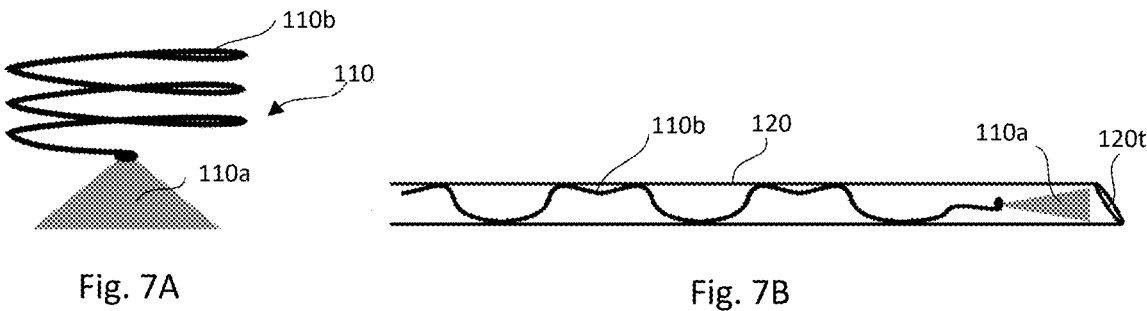
Fig. 7A                    Fig. 7B
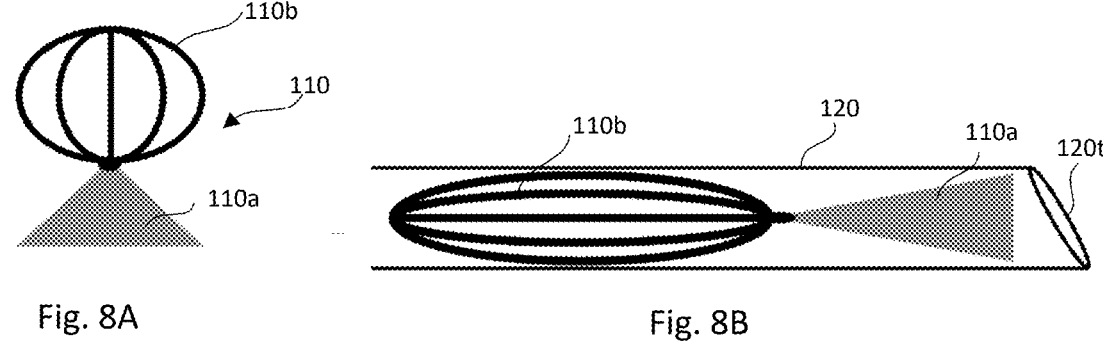
Fig. 8A                    Fig. 8B
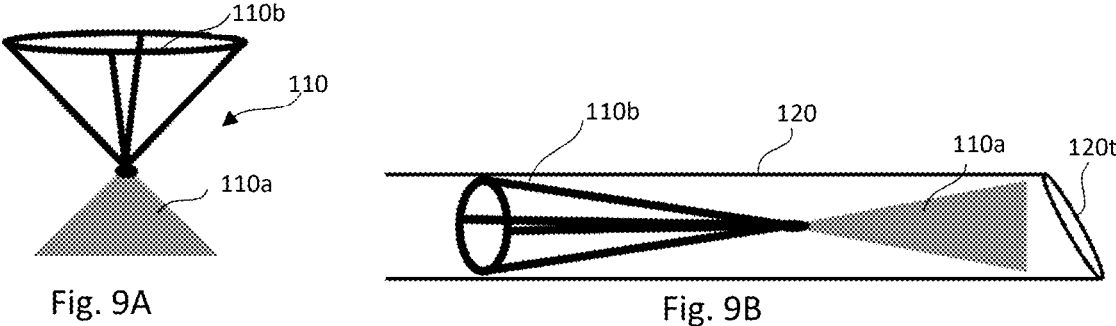
Fig. 9A                    Fig. 9B

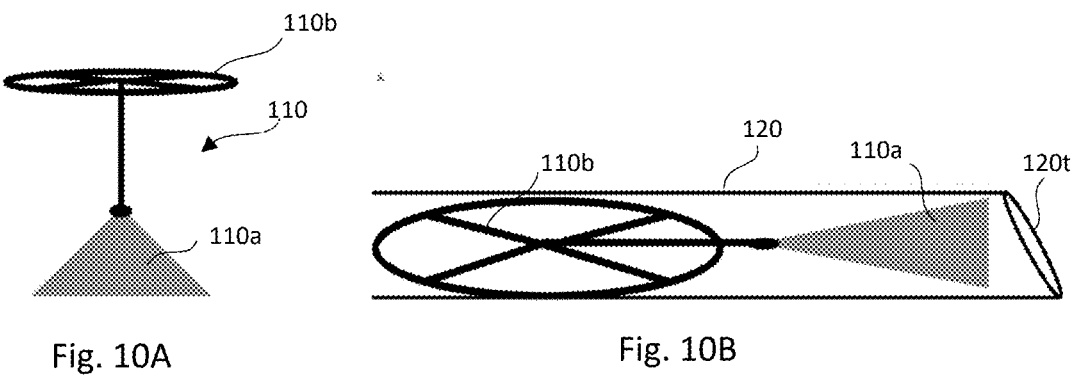
Fig. 10A
Fig. 10B
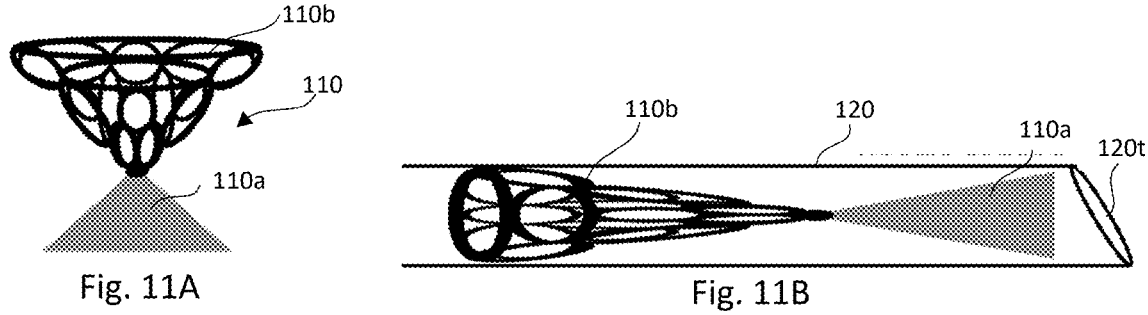
Fig. 11A
Fig. 11B
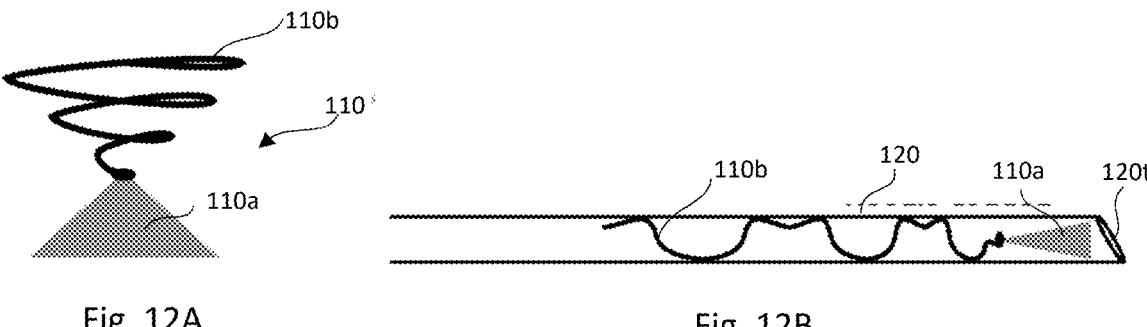
Fig. 12A
Fig. 12B

STRUCTURES FOR INTRACORPOREAL SPACING AND METHODS OF USING SAME

PRIORITY

The present application is a non-provisional of, and claims the benefit of priority under 35 U.S.C. § 119 to, U.S. Provisional Application Ser. No. 62/987,449, filed Mar. 10, 2020, the disclosure of which is herein incorporated herein by reference in its entirety.

FIELD

The present disclosure relates to anchored structures and to methods of intracorporeal spacing using the same.

BACKGROUND

Locally Advanced Pancreatic Cancer (LAPC) patients survive the longest when they receive chemotherapy, surgical resection, and advanced external body radiotherapy, particularly, stereotactic body radiotherapy (SBRT). It is also known that elevating the dose of SBRT can extend survival. There are no SBRT machine limitations to elevating current radiation dose levels, which would likely further extend survival. However, there are other limitations. In this regard, due to the principles underlying radiotherapy, some of the radiation dose is delivered to tissues neighboring a given therapy-targeted tissue (e.g. a tumor). This unintended radiation dose to neighboring tissues, for example, the gastrointestinal (GI) system (e.g. stomach, duodenum, intestines) in the case of a pancreatic tumor, causes toxicity adverse events ranging from vomiting and pain to ulcers and internal bleeding. Higher SBRT doses to the target pancreatic tissue results in higher doses to the gastrointestinal tissue, which causes increased adverse toxicity.

To lower this rate of adverse toxicity events, it would be desirable to lower the unintended dose to tissue adjacent to tissue using blebs (i.e. small masses) of a suitable hydrogel spacing material. However, the inventors believe that two factors may limit the efficacy of such an approach, specifically, when used to separate the stomach from the pancreas. First, hydrogel blebs may relocate after injection and become ineffective for protection. For intense SBRT, patients typically undergo 5-30 sessions on different days. Between the stomach and pancreas, there are tissues with characteristics that vary across the length of the pancreas. In some places, it is connective tissue adhering the two organ walls. In other places, it is a large connective-tissue sac extending further down into the abdomen. If a patient were to receive hydrogel blebs between the stomach-pancreas interface, they will likely walk or otherwise move around between SBRT sessions. This movement will consequently move the stomach and pancreas tissue holding the blebs in place, which will likely force the blebs to relocate further into the sac. Upon returning for further SBRT, the protective GI-spacing will no longer be in place and toxicity events will rise. In contrast, there is no sac between the pancreas and the duodenum (i.e. the curving GI vessel downstream from the stomach) to facilitate this bleb relocation, so injections in this region are less prone to relocation. Second, the stomach tissue may drape in the direction of the pancreas between the multiple, small hydrogel blebs, which would under-protect that tissue. In contrast to the duodenum, where there is a small and relatively stiff pancreas head and duodenum interface, the stomach-pancreas interface is far larger in area and the tissues are perceived to be more flexible, making it more difficult to protect the stomach by positioning multiple masses (blebs) between the stomach and pancreas. As blebs are injected into this stomach-pancreas interface, the stomach and pancreas will likely compress around each bleb. Unless there are multiple blebs covering the entire relevant interface, which could be prohibitive due to the large area, it is likely there will be stomach tissue that drapes down between the blebs and into a higher radiation dose zone.

These and other issues may be addressed by the present disclosure, which pertains to devices and methods that may be employed to protect tissue, including gastrointestinal tissue, by separating such tissue from therapy-targeted tissue using hydrogels and structures that are configured to hold the hydrogels in place.

SUMMARY

In some aspects, the present disclosure pertains to hydrogel-securing structures that comprise anchoring element that is configured to anchor the structure to bodily tissue and a hydrogel-retaining element that is configured to retain a hydrogel mass.

In various embodiments, which may be used in conjunction with the above aspects, the tissue anchoring element may be radiopaque.

In various embodiments, which may be used in conjunction with the above aspects and embodiments, the tissue anchoring element may be bioresorbable.

In various embodiments, which may be used in conjunction with any of the above aspects and embodiments, the tissue anchoring element may comprise an adhesive.

In various embodiments, which may be used in conjunction with any of the above aspects and embodiments, the tissue anchoring element may comprise at least one filament. For example, the at least one filament may be selected from a biostable metal, a bioresorbable metal, a biostable polymer, and a bioresorbable polymer. Alternatively or in addition, the at least one filament may be in the form of at least one curved structure, for example, in the form of an arc or a helix. Alternatively or in addition, the at least one filament may be in the form of at least one tine. Alternatively or in addition, the at least one filament may be a shape memory filament. For instance, the at least one shape memory filament may recover an original shape after being deformed under load and the load may be removed, or the at least one shape memory filament may recover an original shape when ejected a compressed configuration.

In various embodiments, which may be used in conjunction with any of the above aspects and embodiments, the hydrogel-retaining element may be radiopaque.

In various embodiments, which may be used in conjunction with any of the above aspects and embodiments, the hydrogel-retaining element may be bioresorbable.

In various embodiments, which may be used in conjunction with any of the above aspects and embodiments, the hydrogel-retaining element may be biostable metal, a bioresorbable metal, a biostable polymer or a bioresorbable polymer.

In various embodiments, which may be used in conjunction with any of the above aspects and embodiments, the hydrogel-retaining element may comprise one or more filaments.

In various embodiments, which may be used in conjunction with any of the above aspects and embodiments, the hydrogel-retaining element may comprise one or more shape memory filaments.

In various embodiments, which may be used in conjunction with any of the above aspects and embodiments, the hydrogel-retaining element may comprise an expandable scaffold. In some of these embodiments, at least a portion of the expandable scaffold may comprise an overall shape in the form of a spiral (including a helix and a conical spiral), a spheroid, a cone, a disk-shape structure or a random structure. Alternatively or in addition, at least a portion of the expandable scaffold may comprise an overall shape having a shape memory.

In various embodiments, which may be used in conjunction with any of the above aspects and embodiments, the hydrogel-retaining element may comprise a mesh that may be formed from at least one filament. For example, the mesh may be an enclosed mesh having an interior volume and/or the mesh may have an overall disk shape.

In various embodiments, which may be used in conjunction with any of the above aspects and embodiments, the hydrogel-retaining element further comprises a retained hydrogel.

Additional aspects of the present disclosure pertain to kits that comprise (a) a hydrogel-securing structure any of the above aspects and embodiments and (b) a hydrogel or one more precursor fluids that may be crosslinked to form a hydrogel.

In various embodiments, which may be used in conjunction with the above additional aspects, the hydrogel for the kit may comprise one or more monomers selected from ethylene oxide, N-vinyl pyrrolidone, hydroxyethyl acrylate, hydroxyethyl methacrylate, PEG methyl ether acrylate and PEG methyl ether methacrylate.

In various embodiments, which may be used in conjunction with the above additional aspects, the kit may comprise (a) a first precursor fluid that comprises a reactive multi-arm polymer that comprises a plurality of hydrophilic polymeric arms, at least a portion of the hydrophilic polymeric arms comprising one or more reactive end groups and (b) a second precursor fluid that comprises a multifunctional compound that comprises functional groups that are reactive with the reactive end groups of the reactive multi-arm polymer.

Further aspects of the present disclosure pertain to methods that comprise (a) delivering a structure that comprises a hydrogel-retaining element in a body of a subject comprising first and second tissues, such that the hydrogel-retaining element may be disposed between the first tissue of tissue and the second tissue and (b) delivering a hydrogel to the structure, such that the hydrogel is loaded onto and/or into the hydrogel-retaining element and retained in place by the hydrogel-retaining element, and such that the hydrogel is disposed between the first and second tissues thereby separating the first tissue from the second tissue.

In various embodiments, which may be used in conjunction with the above further aspects, the structure comprises an anchoring element, and the anchoring element may be anchored to at least one of the first and second tissues.

In various embodiments, which may be used in conjunction with the above further aspects and embodiments, the hydrogel-retaining element may be an enclosed mesh and the mesh may be filled with the hydrogel.

In various embodiments, which may be used in conjunction with any of the above further aspects and embodiments, hydrogel-retaining element may comprise a scaffold.

In various embodiments, which may be used in conjunction with any of the above further aspects and embodiments, the hydrogel may be a bioresorbable or biostable hydrogel.

In various embodiments, which may be used in conjunction with any of the above further aspects and embodiments, the hydrogel may be delivered as a pre-formed hydrogel, or the hydrogel may be formed from one or more fluids that crosslink in the presence of the hydrogel-retaining element.

In various embodiments, which may be used in conjunction with any of the above further aspects and embodiments, the hydrogel may be administered in the form of a fluid that contains a dispersion of hydrogel particles that may be retained by the hydrogel-retaining element.

In various embodiments, which may be used in conjunction with any of the above further aspects and embodiments, the hydrogel may comprise one or more monomers selected from ethylene oxide, N-vinyl pyrrolidone, hydroxyethyl acrylate, hydroxyethyl methacrylate, PEG methyl ether acrylate and PEG methyl ether methacrylate.

In various embodiments, which may be used in conjunction with any of the above further aspects and embodiments, the hydrogel may comprise a crosslinked product of (a) a reactive multi-arm polymer that comprises a plurality of hydrophilic polymeric arms, at least a portion of the hydrophilic polymeric arms comprising one or more reactive end groups and (b) a multifunctional compound that comprises functional groups that are reactive with the reactive end groups of the reactive multi-arm polymer. In some of these embodiments, the reactive end groups may be electrophilic groups and the functional groups may be nucleophilic groups. In some of these embodiments, the reactive end groups may be selected from N-hydroxysuccinimide esters, imidazole esters, imidazole carboxylates and benzotriazole esters and the functional groups may be selected from amine groups and thiol groups. In some of these embodiments, the hydrophilic polymeric arms of the reactive multi-arm polymer further comprise a hydrolysable ester group.

In various embodiments, which may be used in conjunction with any of the above further aspects and embodiments, the structure and the hydrogel may be delivered through a hollow needle.

In various embodiments, which may be used in conjunction with any of the above further aspects and embodiments, the structure, the hydrogel, or both, may be pushed through needle with a stylet.

In various embodiments, which may be used in conjunction with any of the above further aspects and embodiments, the structure and the hydrogel may be delivered using an endoscope.

In various embodiments, which may be used in conjunction with any of the above further aspects and embodiments, the method may further comprise delivering therapy to the subject such that the first tissue receives more therapy than the second tissue. For example, the therapy may be selected from radiation therapy, proton-based therapy, ultrasonic therapy, ablation therapy, and any other or future energy delivery procedure.

BRIEF DESCRIPTION OF THE DRAWINGS

FIGS. 1A-1B are schematic illustrations of two hydrogel-securing structures, in accordance with two embodiments of the present disclosure.

FIGS. 2A-2D are schematic illustrations of a method of using the structure of FIG. 1B, in accordance with an embodiment of the present disclosure.

FIGS. 3A-3D are schematic illustrations of a method of using the structure of FIG. 1A, in accordance with an embodiment of the present disclosure.

FIG. 4A is a schematic illustration of a hydrogel-securing structure in an unloaded configuration, in accordance with an embodiment of the present disclosure.

FIG. 4B is a schematic illustration of the hydrogel-securing structure of FIG. 4A, loaded into a delivery needle, in accordance with an embodiment of the present disclosure FIG. 5A is a schematic illustration of a hydrogel-securing structure in an unloaded configuration, in accordance with an embodiment of the present disclosure.

FIG. 5B is a schematic illustration of the hydrogel-securing structure of FIG. 5A, loaded into a delivery needle, in accordance with an embodiment of the present disclosure.

FIG. 6A is a schematic illustration of a hydrogel-securing structure in an unloaded configuration, in accordance with an embodiment of the present disclosure.

FIG. 6B is a schematic illustration of the hydrogel-securing structure of FIG. 6A, loaded into a delivery needle, in accordance with an embodiment of the present disclosure.

FIG. 7A is a schematic illustration of a hydrogel-securing structure in an unloaded configuration, in accordance with an embodiment of the present disclosure.

FIG. 7B is a schematic illustration of the hydrogel-securing structure of FIG. 7A, loaded into a delivery needle, in accordance with an embodiment of the present disclosure.

FIG. 8A is a schematic illustration of a hydrogel-securing structure in an unloaded configuration, in accordance with an embodiment of the present disclosure.

FIG. 8B is a schematic illustration of the hydrogel-securing structure of FIG. 8A, loaded into a delivery needle, in accordance with an embodiment of the present disclosure.

FIG. 9A is a schematic illustration of a hydrogel-securing structure in an unloaded configuration, in accordance with an embodiment of the present disclosure.

FIG. 9B is a schematic illustration of the hydrogel-securing structure of FIG. 9A, loaded into a delivery needle, in accordance with an embodiment of the present disclosure.

FIG. 10A is a schematic illustration of a hydrogel-securing structure in an unloaded configuration, in accordance with an embodiment of the present disclosure.

FIG. 10B is a schematic illustration of the hydrogel-securing structure of FIG. 10A, loaded into a delivery needle, in accordance with an embodiment of the present disclosure.

FIG. 11A is a schematic illustration of a hydrogel-securing structure in an unloaded configuration, in accordance with an embodiment of the present disclosure.

FIG. 11B is a schematic illustration of the hydrogel-securing structure of FIG. 11A, loaded into a delivery needle, in accordance with an embodiment of the present disclosure.

FIG. 12A is a schematic illustration of a hydrogel-securing structure in an unloaded configuration, in accordance with an embodiment of the present disclosure.

FIG. 12B is a schematic illustration of the hydrogel-securing structure of FIG. 12A, loaded into a delivery needle, in accordance with an embodiment of the present disclosure.

DETAILED DESCRIPTION

Figure 13:
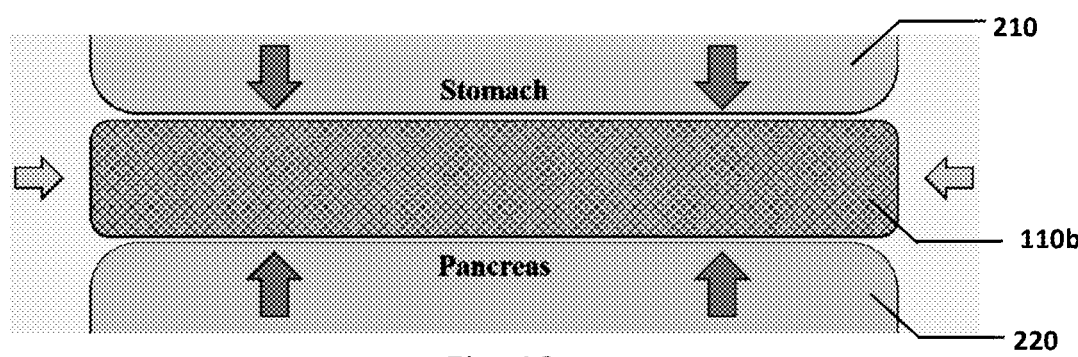
FIG. 13 is a schematic illustration of a hydrogel-filled, hydrogel-retaining element positioned between a stomach and a pancreas, in accordance with an embodiment of the present disclosure.
Figure 14:
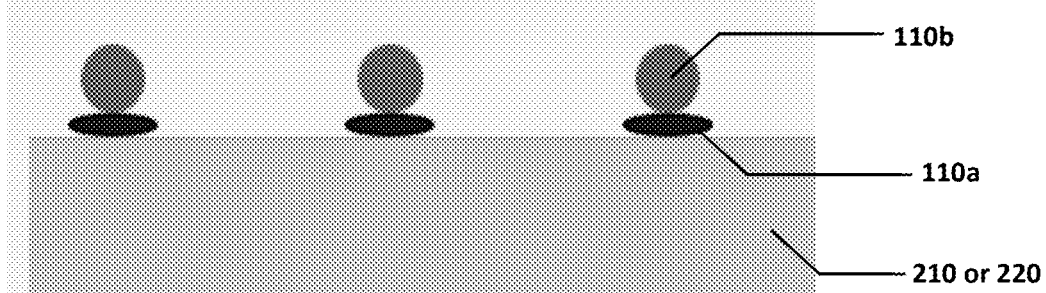
FIG. 14 is a schematic illustration of a hydrogel-filled, hydrogel-securing structure anchored to a pancreas or a stomach, in accordance with an embodiment of the present disclosure.

In various embodiments, for example, to address the problem of relocation, structures with tissue anchoring and hydrogel retention abilities may be delivered to the pancreas-stomach interface prior to hydrogel bleb injection. The anchoring element of the structure will adhere to the wall of the pancreas tissue, the stomach, or both, to resist movement, for example, between energy delivery procedures (e.g. SBRT, EBRT, intensity-modulated radiation therapy, stereotactic radiosurgery, proton-based radiotherapy etc.). After anchoring the structure, the hydrogel material may be injected into/onto the hydrogel-retaining element and the material may engulf and lock itself to the scaffolding element of the structure. In this way, the hydrogel may be attached to the structure and the structure may be attached to tissue, so that the hydrogel resists relocation, allowing it to continue to protect adjacent tissue during treatment.

It is noted that, instead of protecting gastrointestinal tissue from pancreas management, the various hydrogel-securing structures described herein may be used in many tissues to improve the management of many systems. Moreover, while the present disclosure highlights the use of the hydrogel-securing structures to improve SBRT therapy, such structures may also be used to other and future local treatments. For example, various minimally invasive ablation technologies may benefit from the use of such structures, including, for example, microwave ablation, radiofrequency ablation, irreversible electroporation ablation, cryo-based ablation, ultrasound ablation, or any other technology associated with dose leakage into adjacent tissue.

FIGS. 1A and 1B schematically illustrate two embodiments of hydrogel-securing structures 110 in accordance with the present disclosure, each having an anchoring element 110a and a hydrogel-retaining scaffolding element 110b.

As discussed in more detail below, materials that may be used to form the hydrogel-securing structures 110 include metals, polymers and combinations thereof.

Materials that may be used to form the hydrogel-securing structures 110 described herein, including the anchoring elements 110a, hydrogel-retaining scaffolding elements 110b, the hollow hydrogel-retaining elements 110b described further below, may be bioresorbable. Alternatively or in addition, materials that may be used to form such hydrogel-securing structures 110 may be radiopaque. For example, the hydrogel-securing structures 110 may be formed using metals that are in and of themselves radiopaque, or the hydrogel-securing structure 110 may be primarily formed from a non-radiopaque material (e.g., a non-iodinated polymer) and a radiopaque material, either admixed with non-radiopaque material or coated on all or a portion of the non-radiopaque material. In this regard, currently, some pancreas disease patients receive radiopaque fiducial markers injected into the pancreas tissue to improve treatments such as external body radiation therapy (EBRT) or stereotactic body radiation therapy (SBRT). Such markers can be seen on imaging, which allows operators to adjust treatment plans to better locate the disease and better prevent adverse events. The hydrogel-securing structures 110 described herein can be provided with radiopaque properties to replace such markers or to improve the performance of such markers.

Typical procedures for deployment of the hydrogel-securing structures 110 of FIG. 1A and FIG. 1B and associated hydrogel in a patient will now be described in conjunction with the schematic illustrations of FIGS. 2A-2D and FIGS. 3A-3D.

First, the patient may be prepped as necessary for a minimally-invasive stomach-based endoscopic procedure. After prepping, a physician performing the procedure navigates a scope (e.g., an echoendoscope or other suitable endoscope) to the portion of the stomach 210 wall that is adjacent to a tumor treatment zone of the pancreas 220. The physician then pushes a hydrogel-securing structure 110 into a needle 120 of an injection needle catheter or other device such as an aspiration catheter with the anchor element 110a facing the distal tip of the needle 120. (Alternatively, the hydrogel-securing structure 110 may be previously loaded into the needle 120, for example, by a clinician preparing before the procedure or by a third-party (e.g. manufacturer) before clinical handling.) The gauge of the needle is variable and can be, for example, an 18-gauge needle or a 22-gauge needle, among other possibilities.

This process circumferentially squeezes the hydrogel-securing structure 110 temporarily deforming the structure 110 under load (e.g., like a trap of sorts, which can subsequently spring outward into tissue). If desired, the physician may push the needle 120 through a small block of wax to force wax into the needle 120 lumen to lock the hydrogel-securing structure 110 in place, as is common with fiducial marker delivery. The physician then progresses the needle 120 of the injection needle catheter through the working channel and to the end of an echoendoscope (not shown), at which point the needle 120 tip is advanced through the stomach 210 wall, through any additional connective tissue (not shown), through the pancreas-stomach gap 230, and into the pancreas 220 wall as shown in FIGS. 2A and 3A.

Once the needle 120 tip is properly positioned in the pancreas 220 wall, an intra-needle stylet (not shown) may be used to push the hydrogel-securing structure 110 (and wax, if any) slowly out of the needle 120 tip. As the hydrogel-securing structure 110 exits the needle 120 tip, the anchoring element 110a deploys and affixes to the pancreas 220 wall, while the hydrogel-retaining scaffolding element 110b of the hydrogel-securing structure 110 becomes positioned in the pancreas-stomach gap 230 as shown in FIGS. 2B and 3B.

A spacing hydrogel 130 is then injected using a suitable device (in the embodiment shown, the same device 120 used for the delivery of the hydrogel-retaining scaffolding element 110b). For example, the physician may slightly retract the tip of the needle 120 as shown in FIGS. 2B and 3B and load it with a spacing hydrogel 130 as shown in FIGS. 2C and 3C, after which the spacing hydrogel 130 is injected from the needle 120 at the location of the needle tip in the pancreas-stomach gap 230. During injection, a hydrogel bleb 130b will form and intertwine with the hydrogel-retaining scaffolding element 110b of the hydrogel-securing structure 110, thereby locking the hydrogel bleb 130b to the hydrogel-retaining scaffolding element 110b, which is, in turn, locked to the pancreas wall by the anchoring element 110a. In certain embodiments, described in more detail below, the hydrogel may be an in-situ-formed hydrogel that is formed from one or more fluids that crosslink upon injection, further securing the hydrogel bleb 130b to the hydrogel-retaining scaffolding element 110b. This process may be repeated until the physician has determined that enough blebs 230b have been placed for proper tissue protection.

While an endoscopic delivery is illustrated, it should be understood, however, that the present disclosure is not restricted to such delivery, as the hydrogel-securing structure 110 may be delivered by other delivery techniques such as by open surgery, laparoscopy, endovascularly, or percutaneously, among other possibilities.

In the event that the hydrogel-securing structure 110 and/or the hydrogel 130b itself is/are formed using radiopaque materials, the patient can be repeatedly imaged, as needed, to ensure that the hydrogel-securing structures 110 remain in place (e.g., to ensure that the patient has protection throughout multiple ablation procedures.

In the event that the hydrogel-securing structure 110 and the hydrogel blebs 130b are formed using bioresorbable materials, the hydrogel blebs 130b and the hydrogel-securing structure 110 will be absorbed into the body after the procedure(s) has (have) been performed.

Various embodiments will now be described that pertain to various anchoring elements 110a of the hydrogel-securing structures 110 of the present disclosure.

With reference now to FIG. 4A, a hydrogel-securing structure 110 in accordance with the present disclosure is shown in an unloaded configuration (i.e., an unconstrained configuration, for instance, after deployment from a constrained configuration within a needle 120), which includes an anchoring element 110a and a hydrogel-retaining scaffolding element 110b. The hydrogel-retaining scaffolding element 110b is illustrated generically with a shaded circle/oval and can correspond to a wide variety of designs, including those described below in FIGS. 7A-7B, 8A-8B, 9A-9B, 10A-10B, 11A-11B and 12A-12B, among others. The anchoring element 110a in the embodiment shown comprises multiple tines having shape-memory characteristics, which can be used to secure the device to a pancreas wall, among other tissue structures. Although multiple tines are shown which curve back on themselves, other designs are clearly possible. FIG. 4B shows the device of FIG. 4A in a constrained, pre-deployed state while loaded into a needle 120. When loaded into the needle 120, the tines will be manipulated back on each curve so that the tines are extended and the tine tips 110t are closest to the needle opening 120t. Upon deployment, the tines will enter the tissue and at least partially return to the memorized curve shape of FIG. 4A, fixing itself to the tissue.

FIG. 5A is a schematic illustration of a hydrogel-securing structure 110 in accordance with another embodiment of the present disclosure, which is show in an unloaded (i.e., an unconstrained) configuration. The hydrogel-securing structure 110 in includes an anchoring element 110a and a hydrogel-retaining scaffolding element 110b. As with FIGS. 4A-4B, the hydrogel-retaining scaffolding element 110b is illustrated generically with a shaded circle/oval. The anchoring element 110a in the embodiment shown comprises a helical screw having shape-memory characteristics, which can be used to secure the structure 110 to a pancreas wall, among other tissue locations. Other than the single helix design of FIG. 5A, multiple screw designs may be employed as well. FIG. 5B shows the device of FIG. 5A in a constrained, pre-deployed state while loaded into a needle 120. When loaded into the needle 120, the helix may be stretched to reduce the overall radius, with the tip 110t of the helix being positioned closest to the needle opening 120t. Upon deployment, the helix will regain the original helical shape, which can be screwed into the tissue.

FIG. 6A is a schematic illustration of a hydrogel-securing structure 110 in accordance with another embodiment of the present disclosure, which is shown in an unloaded (i.e., an unconstrained) configuration. The hydrogel-securing structure 110 in includes an anchoring element 110a and a hydrogel-retaining scaffolding element 110b. As with FIGS. 4A-4B, the hydrogel-retaining scaffolding element 110b is illustrated generically with a shaded circle/oval. The anchoring element 110a in the embodiment shown comprises a volume of tissue adhesive material. FIG. 6B shows the device of FIG. 6A in a constrained, pre-deployed state while loaded into a needle 120 in which the anchoring element 110a is positioned closest to the needle opening 120t. Depending on the unconstrained width of the volume of tissue adhesive material and the diameter of the lumen of the needle 120, when loaded into the needle 120, the tissue adhesive material may be elongated to reduce the overall width of the same, such that it fits within the lumen of the needle 120. Upon deployment, the tissue adhesive material is brought into contact with tissue and affix itself to the tissue. In addition, where elongated to fit with the lumen of the needle 120, the volume of tissue adhesive material may regain its original shape, depending on the degree of shape memory of the material. In certain embodiments, a tissue adhesive material may be selected that is activated by contact with tissue to help prevent the adhesive from inadvertently affixing to anything before the intended deployment (e.g. inside of the delivery mechanism). Specific examples of adhesive materials include, for example, fibrin glue, cyanoacrylate glue, and gelatin-resorcinol-formaldehyde/glutaraldehyde glues. Such materials are bioresorbable and approved for clinical use, for example, as surgical glues. Alternative tissue adhesive materials include biomimetic tissue adhesives.

Embodiments will now be described that pertain to various hydrogel-retaining scaffolding elements 110b of the hydrogel-securing structures 110 of the present disclosure.

FIG. 7A is a schematic illustration of a hydrogel-securing structure 110 in accordance with an embodiment of the present disclosure, which is show in an unloaded (i.e., an unconstrained) configuration. The hydrogel-securing structure 110 in includes an anchoring element 110a and a hydrogel-retaining scaffolding element 110b. The anchoring element 110a is illustrated generically with a shaded triangle and can correspond to a wide variety of designs, including those described above in FIGS. 4A-4B, 5A-5B, 6A-6B, among others. The hydrogel-retaining scaffolding element 110b in the embodiment shown in FIG. 7A comprises a coil frame, more specifically a helical frame, having shape-memory characteristics, which can be used to secure a subsequently injected hydrogel material. Other than the single helix design of FIG. 7A, multiple other coil designs may be employed as well.

FIG. 7B shows the device of FIG. 7A in a constrained, pre-deployed state while loaded into a needle 120 with the anchoring element 110a being positioned closest to the needle opening 120t. When loaded into the needle 120, the helix may be stretched to reduce the overall radius and thereby fit within the lumen of the needle 120. Upon deployment, the helical frame will regain the original shape and may be positioned, at least partially, in a space between the pancreas and gastrointestinal system of a patient (or any other tissues for which separation is desired). Hydrogel material may then be injected proximate the scaffolding element 110b (e.g., into, onto or around the scaffolding element 110b) with the effect of maintaining the position of the hydrogel relative to the pancreas (or other anchoring tissue).

FIG. 8A is a schematic illustration of a hydrogel-securing structure 110 in accordance with another embodiment of the present disclosure, which includes an anchoring element 110a and a hydrogel-retaining scaffolding element 110b, and which is shown in an unloaded (i.e., an unconstrained) configuration. As with FIGS. 7A-7B, the anchoring element 110a is illustrated generically with a shaded triangle. The hydrogel-retaining scaffolding element 110b in the embodiment shown comprises a spherical frame having shape-memory characteristics. Other than the spherical design of FIG. 8A, multiple other designs may be employed as well, including spheroidal designs besides the vertical-strut embodiment shown, and other spheroids besides spheres, such as oblate and prolate spheroids. FIG. 8B shows the device of FIG. 8A in a constrained, pre-deployed state while loaded into a needle 120 with the anchoring element 110a being positioned closest to the needle opening 120t. When loaded into the needle 120, the spherical frame may be elongated to reduce the overall radius and thereby fit within the lumen of the needle 120. Upon deployment, the spherical frame will regain the original shape and may be positioned, at least partially, in a space between the pancreas and gastrointestinal system of a patient (or any other tissues for which separation is desired). Hydrogel material may then be injected in the space proximate the scaffolding element 110b, thereby maintaining the position of the hydrogel relative to the pancreas (or other anchoring tissue).

FIG. 9A is a schematic illustration of a hydrogel-securing structure 110 in accordance with another embodiment of the present disclosure, which includes an anchoring element 110a and a hydrogel-retaining scaffolding element 110b, and which is shown in an unloaded (i.e., an unconstrained) configuration. As above, the anchoring element 110a is illustrated generically with a shaded triangle. The hydrogel-retaining scaffolding element 110b in the embodiment shown comprises a conical frame having shape-memory characteristics. Beyond the specific design of FIG. 9A, multiple other designs may be employed as well, including conical designs besides the vertical-strut embodiment shown. FIG. 9B shows the device of FIG. 9A in a constrained, pre-deployed state while loaded into a needle 120 with the anchoring element 110a being positioned closest to the needle opening 120t. When loaded into the needle 120, the conical frame may be elongated to reduce the overall radius and thereby fit within the lumen of the needle 120. Upon deployment, the conical frame will regain the original shape and may be positioned, at least partially, in a space between the pancreas and gastrointestinal system of a patient (or any other tissues for which separation is desired). Hydrogel material may then be injected in the space proximate the scaffolding element 110b, thereby maintaining the position of the hydrogel relative to the pancreas (or other anchoring tissue).

FIG. 10A is a schematic illustration of a hydrogel-securing structure 110 in accordance with another embodiment of the present disclosure, which includes an anchoring element 110a and a hydrogel-retaining scaffolding element 110b, and which is shown in an unloaded (i.e., an unconstrained) configuration. As above, the anchoring element 110a is illustrated generically with a shaded triangle. The hydrogel-retaining scaffolding element 110b in the embodiment shown comprises an umbrella-shaped frame having shape-memory characteristics. Beyond the specific design of FIG. 10A, multiple other designs may be employed as well, including umbrella-shaped designs besides those based on a disc-shaped expandable portion as shown. FIG. 10B shows the device of FIG. 10A in a constrained, pre-deployed state while loaded into a needle 120 with the anchoring element 110a being positioned closest to the needle opening 120t. When loaded into the needle 120, the umbrella-shaped frame may be elongated and compressed to reduce the overall radius and thereby fit within the lumen of the needle 120 as shown. Upon deployment, the umbrella-shaped frame will regain the original shape and may be positioned, at least partially, in a space between the pancreas and gastrointestinal system of a patient (or any other tissues for which separation is desired). Hydrogel material may then be injected in the space proximate the scaffolding element 110b, thereby maintaining the position of the hydrogel relative to the pancreas (or other anchoring tissue).

FIG. 11A is a schematic illustration of a hydrogel-securing structure 110 in accordance with another embodiment of the present disclosure, which includes an anchoring element 110a and a hydrogel-retaining scaffolding element 110b, and which is shown in an unloaded (i.e., an unconstrained) configuration. As above, the anchoring element 110a is illustrated generically with a shaded triangle. The hydrogel-retaining scaffolding element 110b in the embodiment shown comprises a meshwork frame having shape-memory characteristics. Beyond the specific design of FIG. 11A, multiple other designs may be employed as well, including meshwork designs besides those based on an overall conic-shaped expandable portion as shown. FIG. 11B shows the device of FIG. 11A in a constrained, pre-deployed state while loaded into a needle 120 with the anchoring element 110a being positioned closest to the needle opening 120t. When loaded into the needle 120, the meshwork frame may be elongated and compressed to reduce the overall radius and thereby fit within the lumen of the needle 120 as shown. Upon deployment, the meshwork frame will regain the original shape and may be positioned, at least partially, in a space between the pancreas and gastrointestinal system of a patient (or any other tissues for which separation is desired). Hydrogel material may then be injected in the space proximate the scaffolding element 110b, thereby maintaining the position of the hydrogel relative to the pancreas (or other anchoring tissue).

FIG. 12A is a schematic illustration of a hydrogel-securing structure 110 in accordance with another embodiment of the present disclosure, which includes an anchoring element 110a and a hydrogel-retaining scaffolding element 110b, and which is shown in an unloaded (i.e., an unconstrained) configuration. As above, the anchoring element 110a is illustrated generically with a shaded triangle. The hydrogel-retaining scaffolding element 110b in the embodiment shown comprises a spiral frame having shape-memory characteristics. Beyond the specific design of FIG. 12A, multiple other designs may be employed as well, including spiral designs besides those based on an overall conic-shaped spiral design as shown, including helical spirals. FIG. 12B shows the device of FIG. 12A in a constrained, pre-deployed state while loaded into a needle 120 with the anchoring element 110a being positioned closest to the needle opening 120t. When loaded into the needle 120, the spiral frame may be elongated and compressed to reduce the overall radius and thereby fit within the lumen of the needle 120 as shown. Upon deployment, the spiral frame will regain the original shape and may be positioned, at least partially, in a space between the pancreas and gastrointestinal system of a patient (or any other tissues for which separation is desired). Hydrogel material may then be injected in the space proximate the scaffolding element 110b, thereby maintaining the position of the hydrogel relative to the pancreas (or other anchoring tissue).

Dimensions for the hydrogel-retaining scaffolding elements 110b of the present disclosure may vary widely, with typical unloaded sizes ranging from 0.2 to 5 cm in height and from 0.2 to 5 cm in width.

It should be noted that while various hydrogel-securing structure 110 are described herein that contain a single anchoring element 110a, other embodiments may contain two or more anchoring elements 110a. Moreover, while various hydrogel-securing structure 110 are described herein that contain a single hydrogel-retaining scaffolding element 110b, other embodiments may contain two or more hydrogel-retaining scaffolding elements 110b.

Various embodiments are also provided herein in which hydrogel-securing structures are employed which comprise a hollow hydrogel-retaining element that provides a large, continuous hydrogel mass, ensuring consistent spacing between neighboring tissue such as the stomach and the pancreas. In various embodiments, such hydrogel-securing structures may further comprise one or more anchoring elements, which help keep the hollow hydrogel-retaining element in place.

As with the hydrogel-retaining scaffolding elements described above, the hollow hydrogel-retaining elements described herein, as well as any anchoring elements associated with the hollow hydrogel-retaining elements, may be bioresorbable, radiopaque, or both.

One embodiment is schematically illustrated in FIG. 13, which show a hollow hydrogel-retaining element 110b containing a continuous hydrogel mass, in which the hydrogel-retaining element 110b and the hydrogel within it provide resistance to the pressure exerted by the stomach 210 and pancreas 220 against one another. In the embodiment shown, the hollow hydrogel-retaining element 110b may be in the form of a hollow mesh. In certain embodiments, an expandable mesh may be provided which exerts tension on the hydrogel, resisting deformation of the hydrogel due to any pressure exerted on it by the stomach 210 and pancreas 220, ensuring spacing.

In these embodiments, the mesh and hydrogel may form an overall disk-shaped hydrogel-securing structure when the mesh is expanded with the hydrogel. Preferably, the thickness of the disk expands as the mesh is filled with the hydrogel, while at the same time limiting radial expansion. The mesh that is selected is beneficially sufficiently fine, such that any injected hydrogel will not leak through the gaps in the mesh when the mesh is expanded. This parameter will be dependent on properties the specific hydrogel chosen.

As noted above, to prevent the mesh-hydrogel system from moving within the abdomen, the mesh-hydrogel system may be anchored to the stomach, the pancreas, or both. Several possible anchoring embodiments are discussed below.

Figure 16:
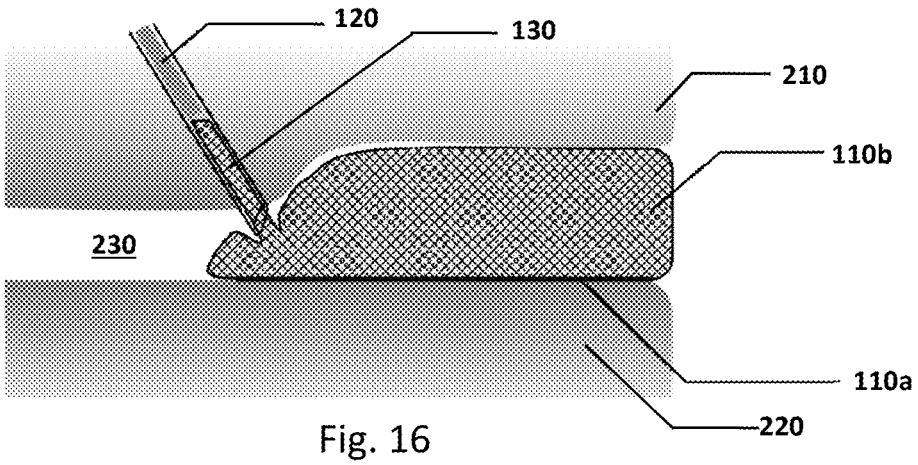
FIG. 16 is a schematic illustration of a method of providing a hydrogel-filled, hydrogel-retaining element between a stomach and a pancreas, in accordance with an embodiment of the present disclosure.

For example, with reference to FIG. 16, a biocompatible adhesive 110a may be applied to a hollow hydrogel-retaining element 110b prior to deployment which is then delivered and affixed to a surface of the target tissues, for example the pancreas 220 and/or stomach 210, after which the hollow hydrogel-retaining element 110b is filled with hydrogel.

In other embodiments such as that shown in FIG. 4, an adhesive 110a may be delivered to the tissue prior to delivery of the hollow hydrogel-retaining element 110b. For example, in the case where the hollow hydrogel-retaining element 110b is a mesh, prior delivery of the adhesive 110a may prevent self-adhesion or entanglement of the mesh. The adhesive may be delivered via the same device that is used to deliver the mesh to the target site.

Figure 15:
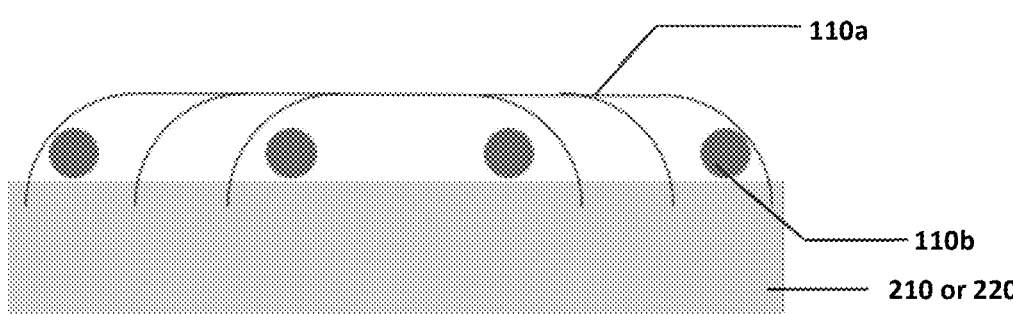
FIG. 15 is a schematic illustration of a hydrogel-filled, hydrogel-securing structure anchored to a pancreas or a stomach, in accordance with an embodiment of the present disclosure.

In still other embodiments, one or more tines 110a (e.g., staples) may be employed which cover one or more filaments of the mesh 110b and penetrate into tissue of the pancreas 220 or stomach 210 as shown in FIG. 15. For example, one or more tines 110a may be employed to anchor the mesh 110b to the pancreas 220 nearest a tumor in the pancreas, where spacing is of utmost importance. Like the mesh 110b, the tines 110a may be bioresorbable, radiopaque or both.

Dimensions for the hollow hydrogel-retaining elements of the present disclosure, including meshes, will vary with the implantation site. Where the hollow hydrogel-retaining element is used to separate a tumor from the stomach, the dimensions for the expanded hollow hydrogel-retaining element may range, for example, from 0.5 to 5 cm in height, typically, 1 to 3 cm in height, and have a width ranging from about 1 to 5 times the height, among other possibilities.

A typical procedure for deployment of a mesh-hydrogel system in a patient will now be described in conjunction with the schematic illustration of FIG. 16.

First, the patient may be prepped as necessary for a mild, minimally-invasive stomach-based endoscopic procedure. After prepping, the physician performing the procedure navigates an echoendoscope (not shown) to a portion of the stomach 210 wall that is adjacent to the tumor treatment zone of the pancreas 220. The physician then progresses a needle 120 through the working channel of the echoendoscope, through the stomach wall, and likely through additional connective tissue.

The physician then pushes a mesh 110b through the needle 120 and into a desired space 230 between the stomach 210 and the pancreas 220 using a stylet (not shown). If a tined anchoring method is used, one or more tines will be advanced through the needle 120 via a stylet and delivered over the mesh 110b and into the pancreas 220, locking the mesh 110b into place.

The physician may then load the needle 120 with hydrogel 130. The physician then advances the hydrogel 130 through the needle 120 and injects the hydrogel 130 into the pancreas-stomach gap 230. During injection, a mass of the hydrogel 130 will form and expand within the earlier-placed mesh 110b.

In some embodiments, the mesh is at least partially filled with hydrogel 130 at the time of delivery to give the mesh shape. Additional hydrogel may be added afterward to fill the mesh 110b with the hydrogel 130. In some embodiments, the needle 120 may be at an angle to and at a proximal side of the tumor such that the mesh-hydrogel system expands toward the tumor.

As noted above, the hydrogel-securing structures 110 described herein, including the anchoring elements 110a, hydrogel-retaining scaffolding elements 110b, and the hollow hydrogel-retaining elements 110b described herein, may be formed using materials that are in and of themselves radiopaque, or the hydrogel-securing structures 110 may be primarily formed from a non-radiopaque material (e.g., non-iodinated polymers) and a radiopaque material either admixed with non-radiopaque material that forms the hydrogel-securing structure 110 or coated on all or a portion of the non-radiopaque material that forms the hydrogel-securing structure 110. As also noted above, all or part of the hydrogel-securing structures 110 described herein, may be formed from bioresorbable materials, making them temporary.

Such temporary hydrogel-securing structures 110 may be designed to maintain sufficient form and function until after a given treatment schedule is complete. In addition, if the structure is paired with a bioresorbable hydrogel 130, then the hydrogel-securing structures 110 and hydrogel 130 can both break down leaving no (or minimal) materials behind.

Various materials for use in conjunction with the present disclosure will now be described.

Materials for the tines and hydrogel-retaining scaffolding elements described herein include various shape-memory metals including nickel-titanium alloys or other polycrystalline or lightweight alloys such as copper-, iron-, cobalt-, nickel-, titanium-, magnesium-, and aluminum-based options, among others. Materials for the tines and hydrogel-retaining scaffolding elements described herein further include magnesium-based metals with shape memory. See, e.g., Daniel J. Hoh, M.D., et. al., "Shape Memory Alloys: Metallurgy, Biocompatibility, and Biomechanics for Neurosurgical Applications," Operative Neurosurgery, Volume 64, Issue suppl_5, 1 May 2009, Pages ons199-ons214 and Yukiko Ogawa et al., "A lightweight shape-memory magnesium alloy," Science 22 Jul. 2016: Vol. 353, Issue 6297, pp. 368-370. Materials for the hydrogel-retaining scaffolding elements also include shape-memory polymers. In this regard, various bioresorbable shape-memory polymers exist including bioresorbable shape-memory polymers based on poly(propylene carbonate) (PPC), poly(ε-caprolactone) (PCL), oligo (ε-caprolactone) (OCL), polyurethane, poly (lactide-co-glycolide) (PLGA), and poly(ethylene glycol) (PEG), among others.

To improve performance (e.g., improve adhesion, improve biocompatibility, improve safety, improve efficacy of spacing, provide additional therapeutics, etc.), the hydrogel-securing structures 110 described herein may be provided with a variety of coatings. For example to improve adhesion between the hydrogel and the hydrogel-retaining elements 110b of the hydrogel-securing structures 110 described herein, the hydrogel-retaining elements 110b may be coated with a polymer comprising one or more monomers that correspond to one or more monomers of the hydrogel. For example, where the hydrogel comprises ethylene oxide, the hydrogel-retaining elements 110b can be coated with a polymer comprising ethylene oxide (e.g., PEO); where the hydrogel comprises N-vinyl pyrrolidone, the hydrogel-retaining elements 110b can be coated with a polymer comprising N-vinyl pyrrolidone; where the hydrogel comprises hydroxyethyl acrylate, the hydrogel-retaining elements 110b can be coated with a polymer comprising hydroxyethyl acrylate; where the hydrogel comprises hydroxyethyl methacrylate, the hydrogel-retaining elements 110b can be coated with a polymer comprising hydroxyethyl methacrylate; and so forth. Alternatively or in addition, the hydrogel-securing structures 110 described herein may also be provided with coatings such as bland coatings, stealth coatings, drug-eluting coatings, etc. For examples of coatings that enhance biocompatibility, see, e.g., O.F. Bertrand et al., "Biocompatibility aspects of new stent technology." J. Am. Coll. Cardiol., 32 (3) (1998), pp. 562-571 and P. Mandracci et al., "Surface treatments and functional coatings for biocompatibility improvement and bacterial adhesion reduction in dental implantology," Coatings 6 (1) (2016), pp. 1-22.

Hydrogel materials for use herein include biostable and bioerodable hydrogels and may be pre-formed hydrogels or in-situ formed hydrogels, which may be formed from one or more fluids that crosslink upon injection.

In certain embodiments, the hydrogel materials may include a crosslinked product of (a) a reactive multi-arm polymer that comprises a core region and a plurality of hydrophilic polymeric arms comprising one or more reactive end groups and (b) a multifunctional compound that comprises functional groups that are reactive with the reactive end groups of the reactive multi-arm polymer.

The hydrophilic polymeric arms may be formed from one or more hydrophilic monomers, examples of which can be selected from ethylene oxide, N-vinyl pyrrolidone, hydroxyethyl acrylate, hydroxyethyl methacrylate, PEG methyl ether acrylate and PEG methyl ether methacrylate. In some embodiments, the hydrophilic polymeric arms may comprise a hydrolysable ester group.

In some embodiments, the reactive end groups may be electrophilic groups and the functional groups may be nucleophilic groups. In some embodiments, the reactive end groups may be selected from N-hydroxysuccinimide esters, imidazole esters, imidazole carboxylates and benzotriazole esters, and the functional groups may be selected from amine groups and thiol groups.

In some embodiments, the reactive multi-arm polymer may comprise a core region and a plurality of hydrophilic polymeric arms that comprise polyethylene oxide and a succinimidyl ester group linked to the hydrophilic polymeric arms by a hydrolysable ester.

In some embodiments, the core region comprises a residue of a polyol that is used to form the polymeric arms. Illustrative polyols may be selected, for example, from straight-chained, branched and cyclic aliphatic polyols including straight-chained, branched and cyclic polyhydroxyalkanes, straight-chained, branched and cyclic polyhydroxy ethers, including polyhydroxy polyethers, straight-chained, branched and cyclic polyhydroxyalkyl ethers, including polyhydroxyalkyl polyethers, straight-chained, branched and cyclic sugars and sugar alcohols, such as glycerol, mannitol, sorbitol, inositol, xylitol, quebrachitol, threitol, arabitol, erythritol, adonitol, dulcitol, fucose, ribose, arabinose, xylose, lyxose, rhamnose, galactose, glucose, fructose, sorbose, mannose, pyranose, altrose, talose, tagatose, pyranosides, sucrose, lactose, and maltose, oligomers (defined herein as ranging from two to ten units, including dimers, trimers, tetramers, pentamers, hexamers, heptamers, octamers, enneamers and decamers) of straight-chained, branched and cyclic sugars and sugar alcohols, polymers (defined herein as eleven or more units) of straight-chained, branched and cyclic sugars and sugar alcohols, including the preceding sugars and sugar alcohols, starches, amylose, dextrins, cyclodextrins, as well as polyhydroxy crown ethers, and polyhydroxyalkyl crown ethers. In certain beneficial embodiments, the polyol is an oligomer of a sugar alcohol such as glycerol, mannitol, sorbitol, inositol, xylitol, or erythritol, among others. In certain beneficial embodiments, the polyol may contain three or more hydroxyl groups, for example, between four and twelve hydroxyl groups in certain cases.

In some embodiments, the multifunctional compound may by comprise multiple amine functional groups. Particular examples of multifunctional amines which may be used as the multifunctional compound include trilysine, ethylenetriamine, diethylene triamine, hexamethylenetriamine, di(heptamethylene) triamine, di(trimethylene) triamine, bis (hexamethylene) triamine, triethylene tetramine, tripropylene tetramine, tetraethylene pentamine, hexamethylene heptamine, pentaethylene hexamine, dimethyl octylamine, and dimethyl decylamine, and JEFFAMINE' polyetheramines available from Huntsman Corporation, among others.

Hydrogel materials for use herein include polyethylene glycol (PEG)-based hydrogels such as SpaceOAR®, a longterm bioresorbable injectable hydrogel based on multi-arm PEG, which has been used to create or maintain space between the prostate and rectum in order to reduce side effects of off-target radiation therapy, and TraceIT® hydrogel, a bioerodible injectable synthetic hydrogel consisting primarily of water and iodinated cross-linked polyethylene glycol (PEG). See "Augmenix Announces Positive Three-year SpaceOAR Clinical Trial Results," *Imaging Technology News*, Oct. 27, 2016 and "Augmenix Receives FDA Clearance to Market its TraceIT™ Tissue Marker," *BusinessWire* Jan. 28, 2013.

In some embodiments, recently developed hydrogels with tissue adhesion properties may be used, which may eliminate the need for a separate anchoring mechanism. See, e.g., Lu Han et al., "Tough, self-healable and tissue-adhesive hydrogel with tunable multifunctionality," *Nature, NPG Asia Mater* 9, e372 (2017) doi:10.1038/am.2017.33. In embodiments where the hydrogel-retaining element is a mesh, such hydrogels may be directly loaded into the mesh without additional anchoring steps.

Mesh materials for use in the present disclosure include various mesh materials that are able to be woven into threads (and thus form a mesh) and that are sufficiently strong to overcome the force exerted on the mesh by outward expansion of hydrogel. Specific materials include biostable and bioresorbable mesh materials which may be selected, for example, from polypropylene, polyethylene terephthalate, polytetrafluorethylene, and poly(lactic acid), among others, including various other materials known for use in surgical mesh applications.

Adhesives for use in the present disclosure include fibrin glue, gelatin-resorcinol-formaldehyde/glutaraldehyde adhesives, and various surgical adhesives including octyl-cyanoacrylate adhesives and other adhesives that have the ability to set and hold under moist conditions, are quick setting and are bioresorbable over an extended time frame. See, e.g., Vrushali Bhagat and Matthew L. Becker, 'Degradable Adhesives for Surgery and Tissue Engineering," Biomacromolecules 2017, 18, 10, 3009-3039.

Variations, modifications, and other implementations of the present disclosure in addition to the various embodiments described herein will occur to those of ordinary skill in the art.

The invention claimed is:

1. A hydrogel-securing structure comprising a tissue anchoring element that is configured to anchor the structure to a first tissue and a hydrogel-retaining element that is configured to retain a hydrogel mass after the hydrogel-securing structure is anchored to the first tissue, wherein the tissue anchoring element comprises multiple filaments in the form of multiple tines and is configured to secure the device to the first tissue, wherein the hydrogel-retaining element comprises one or more shape-memory filaments, wherein the hydrogel-retaining element is configured to be positioned between a second tissue and the first tissue, wherein the hydrogel-retaining element is bioresorbable.

2. The hydrogel-securing structure of claim 1, wherein the tissue anchoring element is radiopaque, bioresorbable, or both.

3. The hydrogel-securing structure of claim 1, wherein the tissue anchoring element comprises an adhesive.

4. The hydrogel-securing structure of claim 1, wherein the multiple filaments are in the form of multiple curved structures.

5. The hydrogel-securing structure of claim 1, wherein the multiple filaments are shape-memory filaments.

6. The hydrogel-securing structure of claim 1, wherein the hydrogel-retaining element comprises an expandable scaffold that comprises the one or more shape memory filaments.

7. The hydrogel-securing structure of claim 6, wherein at least a portion of the expandable scaffold comprises an overall shape having a shape memory.

8. The hydrogel-securing structure of claim 1, wherein the hydrogel-retaining element comprises a mesh that is formed from the one or more shape-memory filaments.

9. The hydrogel-securing structure of claim 8, wherein the mesh is an enclosed mesh having an interior volume.

10. The hydrogel-securing structure of claim 1, wherein the first tissue is the pancreas wall and the second tissue is the stomach wall.

11. The hydrogel-securing structure of claim 1, wherein the first tissue is the stomach wall and the second tissue is the pancreas wall.

12. A kit comprising (a) a hydrogel-securing structure in accordance with claim 1 and (b) a hydrogel or one more precursor fluids that are crosslinked to form a hydrogel.

13. The kit of claim 12, wherein the hydrogel comprises one or more monomers selected from ethylene oxide, N-vinyl pyrrolidone, hydroxyethyl acrylate, hydroxyethyl methacrylate, PEG methyl ether acrylate and PEG methyl ether methacrylate.

14. The kit of claim 12, comprising (a) a first precursor fluid that comprises a reactive multi-arm polymer that comprises a plurality of hydrophilic polymeric arms, at least a portion of the hydrophilic polymeric arms comprising one or more reactive end groups and (b) a second precursor fluid that comprises a multifunctional compound that comprises functional groups that are reactive with the reactive end groups of the reactive multi-arm polymer.

15. A hydrogel-securing structure comprising a tissue anchoring element that is configured to anchor the structure to a first tissue and a hydrogel-retaining element that is configured to retain a hydrogel mass after the hydrogel-securing structure is anchored to the first tissue, wherein the tissue anchoring element comprises multiple filaments in the form of multiple tines and is configured to secure the device to the first tissue, wherein the hydrogel-retaining element comprises one or more shape-memory filaments, wherein the hydrogel-retaining element is configured to be positioned between a second tissue and the first tissue, and wherein the hydrogel-retaining element further comprises a retained hydrogel.

16. A method comprising (a) delivering a hydrogel-securing structure that comprises a tissue anchoring element that is configured to anchor the hydrogel-securing structure to bodily tissue and a hydrogel-retaining element in a body of a subject comprising first and second tissues, such that the hydrogel-retaining element is disposed between the first tissue and the second tissue; and (b) delivering a hydrogel to the hydrogel-securing structure such that the hydrogel is loaded onto and/or into the hydrogel-retaining element and is retained in place by the hydrogel-retaining element, and such that the hydrogel is disposed between the first and second tissues thereby separating the first tissue from the second tissue, wherein the tissue anchoring element comprises at least one filament in the form of at least one tine, and wherein the hydrogel-retaining element comprises one or more shape-memory filaments.

17. The method of claim 16, wherein the hydrogel-securing structure and the hydrogel are delivered through a hollow needle.

18. The method of claim 16, further comprising delivering energy based therapy to the subject such that the first tissue receives more energy based therapy than the second tissue.

19. The method of claim 16, wherein the tissue anchoring element is anchored to the pancreas wall or the stomach wall.

* * * * *